(12) United States Patent
Norcini et al.

(10) Patent No.: US 7,230,121 B2
(45) Date of Patent: Jun. 12, 2007

(54) SULFONIUN SALTS, METHODS FOR THEIR PREPARATION AND USE THEREOF AS PHOTOINITIATORS FOR RADIATION CURABLE SYSTEMS

(75) Inventors: Gabriele Norcini, Comabbio (IT); Angelo Casiraghi, Milan (IT); Marco Visconti, Varese (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 463 days.

(21) Appl. No.: 10/484,358

(22) PCT Filed: Jul. 4, 2002

(86) PCT No.: PCT/EP02/07415

§ 371 (c)(1),
(2), (4) Date: Jun. 22, 2004

(87) PCT Pub. No.: WO03/008404

PCT Pub. Date: Jan. 30, 2003

(65) Prior Publication Data

US 2004/0242901 A1   Dec. 2, 2004

(30) Foreign Application Priority Data

Jul. 19, 2001 (IT) .......................... MI2001A1543
Jul. 19, 2001 (IT) .......................... MI2001A1544

(51) Int. Cl.
*C07F 9/68* (2006.01)
*C07F 9/6553* (2006.01)

(52) U.S. Cl. ................... 549/3; 549/23; 548/2; 548/10; 556/64; 522/22

(58) Field of Classification Search ................ 556/64; 522/31, 22; 549/3, 23; 546/2, 10; 548/2, 548/10

See application file for complete search history.

(56) References Cited

U.S. PATENT DOCUMENTS

| 4,684,671 A | 8/1987 | Tsuchiya et al. ............... 522/31 |
| 5,731,364 A | 3/1998 | Sinta et al. ................... 522/31 |
| 2005/0176969 A1* | 8/2005 | Herlihy et al. ................. 549/3 |

FOREIGN PATENT DOCUMENTS

| EP | 0580552 A1 | 7/1993 |
| EP | 0869393 A1 | 10/1998 |

OTHER PUBLICATIONS

4 Chemistry, Excited-State Processes, and Reactivity of CationicPhotoinitiators, 4-2 Onium Salts, pp. 103-115, 4 Figs., 4 Tables.

* cited by examiner

*Primary Examiner*—Porfirio Nazario-Gonzalez
(74) *Attorney, Agent, or Firm*—Madan, Mossman & Sriram, P.C.

(57) ABSTRACT

The present invention relates to sulfonium salts, to methods for their preparation and to radiation curable compositions containing them as photoinitiators.

24 Claims, No Drawings

SULFONIUN SALTS, METHODS FOR THEIR PREPARATION AND USE THEREOF AS PHOTOINITIATORS FOR RADIATION CURABLE SYSTEMS

FIELD OF THE INVENTION

The invention relates to sulfonium salts, to methods for their preparation, to formulations containing them and to their use as photoinitiators for radiation curable systems.

STATE OF THE ART

The increasing utilisation of UV-visible curable systems arises from some of its advantages such as the high speed of formation of the coating, its good adhesion to plastics and metals and its high flexibility.

In addition the very low level of extractable material and the absence of odour are two important properties of these systems.

These curable systems generally contain a cationic polymerisable material and an onium salt (sulfonium, phosphonium, iodonium salts) eventually dissolved in a reactive solvent.

Sulfonium salts can be utilised as initiators of cationic polymerisation after photochemical activation.

It is well known that these compounds are acid generators suitable for the polymerisation of epoxy or vinyl monomers.

It is also known that some problems are encountered in the use of sulfonium salts, e.g. their low solubility in formulations and the release of in the curing process.

Sulfonium salts possess a low solubility in non polar media, such as in the epoxy or vinyl monomers based formulations, and it is necessary to dissolve them in advance before use; many attempts have been made to increase their solubility, as reported in J. P. Fouassier "Photoinitiation, photopolymerisation and photocuring" (Hanse Publisher).

In the same book it is reported that cationic polymerisation takes place also in the presence of oxygen and after irradiation ("dark reaction"); a thermal post curing is often required to increase the polymerisation degree.

As it is reported in U.S. Pat. No. 4,684,671, the photolytic breaking of the C—$S^+$ bond in sulfonium salts during their irradiation is a further well known feature leading to the formation of low molecular weight compounds (such as benzene).

The release of toxic and/or volatile compounds must be avoided especially when the photopolymerisable formulations are used in food packaging.

To overcome this particular problem iodonium salts with high molecular weight were proposed, as well as substituted sulfonium salts (U.S. Pat. No. 4,684,671); nonetheless, after irradiation, the concentration of benzene in the coating was about 150-200 ppm.

Heterocyclic ring containing a sulfonium salt in their structures were utilised as initiators of polymerisation activated by light or heat.

In EP 580552 the use of compounds of formula (A) together with the more traditional sulfonium salts of formula (B) is reported,

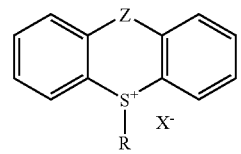

(A)

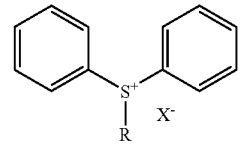

(B)

wherein:

R is a $C_5$-$C_8$ cycloalkyl substituted with another $C_5$-$C_8$ cycloalkyl radical;

X is an anion selected from: $PF_6^-$, $AsF_6^-$, $SbF_6^-$, $SbF_5OH^-$;

Z is selected from: single bond, oxygen, sulfur, a group of formula >$S^+R$ $X^-$, a group of formula >C=O.

The above-described compounds act as heat-sensitive initiators for cationic polymerisation.

Sulfonium salts are also utilised as photoinitiators for resists.

In U.S. Pat. No. 5,731,364 a photo resist containing tri-arylsulfonium salts, tri-aryldisulfonium salts and salts of formula (C) and (D) is described,

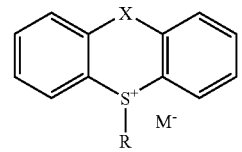

(C)

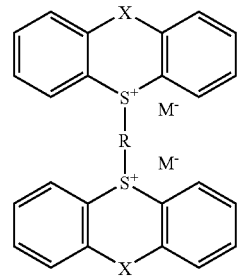

(D)

wherein:

$M^-$ is a carboxylate or an organic sulfonate anion;

R is an unsubstituted or substituted aryl group;

X is O, S, N—R or a $C_1$-$C_3$alkylene.

In EP 869393 a photo resist composition containing as photoinitiators diarylalkylsulfonium salts or thianthrenium derivatives wherein the anion is benzenesulfonate, anthracenesulfonate or naphtalenesulfonate is described.

In U.S. Pat. No. 4,161,478 photoinitiators of formula (E) are reported,

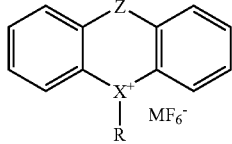

(E)

wherein:

M is selected from: P, As, Sb;

X is S or Se;

R is an aryl;

Z is selected from: S, SO, $CH_2$, $C_2H_4$, NR' wherein R' is $C_1$-$C_8$ alkyl or $C_6$-$C_{13}$ aryl.

The compounds of formula (E) are cationic photoinitiators for a variety of monomers and oligomers.

In the above-mentioned publications the problem of the emission of benzene from triarylsulfonium salts when irradiated is never considered.

There thus exists a need in the art for sulfonium salts acting as photoinitiators for cationic polymerisation exhibiting a good solubility in the formulations without the drawbacks of the known sulfonium salts, such as the release of undesired compounds (e.g. benzene), especially useful in food packaging.

SUMMARY OF THE INVENTION

It has now been found a new class of sulfonium salts releasing less than 1 ppm of benzene when used as cationic photoinitiators for compositions curable by exposure to UV-visible light.

The present invention is directed to sulfonium salts of the general formula (I):

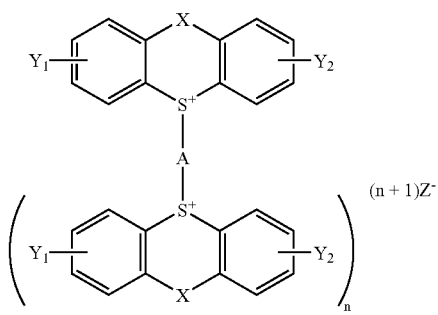

(I)

wherein:

n is 1 or 2;

X is selected from: S, O, $CH_2$, CO, single bond, N—R wherein R is H, or alkyl or aryl;

$Y_1$ and $Y_2$ are equal or different and are selected from: H, $C_1$-$C_6$ linear or branched alkyl, cycloalkyl, O-alkyl, hydroxyl, halogen, S-alkyl, S-aryl;

$Z^-$ is a group of the general formula $MQ_p$ wherein M is B, P, As or Sb; Q is F, Cl, Br, I, or perfluorophenyl; p is an integer from 4 to 6;

A is a functional group of the general formula (II):

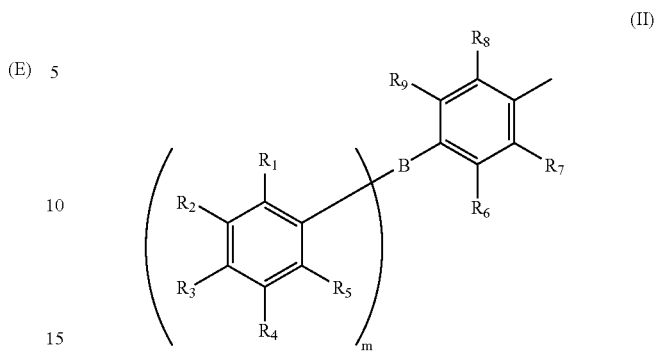

(II)

carrying two or three sulfonium salts units, wherein:

m is 1 or 2;

$R_1$-$R_9$ are equal or different and are selected from: single bond, H, halogen atom (F, Cl, Br, I), nitro, $C_1$-$C_6$ linear or branched alkyl, $C_1$-$C_6$ linear or branched alkoxyl, S—$C_1$-$C_6$ linear or branched alkylthio, with the proviso that at least one of $R_1$-$R_5$ is H;

when m=1, B is selected from: O; S; SO;$SO_2$; $CH_2$; single bond; NR (wherein R is H, $C_1$-$C_6$ linear or branched alkyl); $C_2$-$C_{18}$ linear or branched alkylene carrying at its ends two heteroatoms, equal or different, selected from O, S, N—R the alkylene being eventually substituted with $C_1$-$C_6$ linear or branched hydroxyalkyl, $C_1$-$C_6$ linear or branched mercaptoalkyl, hydroxyl, amino or aminoalkyl; an alicyclic group containing two nitrogen atoms in the ring, the alicyclic group being eventually substituted with OH, $NH_2$, $C_1$-$C_6$ linear or branched aminoalkyl;

when m=2, B is selected from N; a $C_3$-$C_{18}$ linear or branched alkyl carrying three heteroatoms, equal or different selected from O, S, N—R, the alkyl being eventually substituted with $C_1$-$C_6$ hydroxyalkyl, $C_1$-$C_6$ mercaptoalkyl, hydroxyl, amino or aminoalkyl; an alicyclic group with three N in the ring, the alicyclic group being eventually substituted with OH, $NH_2$, $C_1$-$C_6$ linear or branched aminoalkyl.

The present invention is also directed to the sulfonium salts of formula (III):

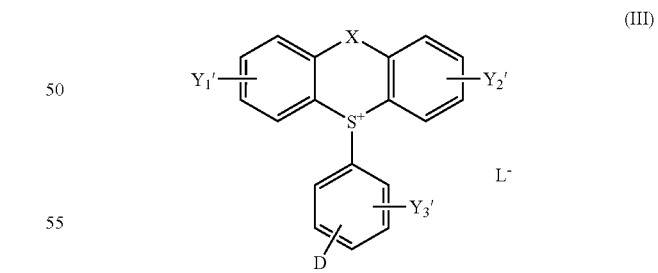

(III)

wherein:

X is selected from: S, O, $CH_2$, CO, single bond, N—R wherein R is H, or alkyl or aryl;

$Y_1'$, $Y_2'$, $Y_3'$ are equal or different and are selected from: H, $C_1$-$C_6$ linear or branched alkyl, cycloalkyl, O-alkyl, hydroxyl, halogen, S-alkyl, S-aryl, $NR_1R_2$ wherein $R_1$ and $R_2$ are equal or different and are selected from H, linear or branched alkyl, cycloalkyl, aryl;

L⁻ is a group of the general formula $MQ_p$ wherein M is B, P, As or Sb;

Q is F, Cl, Br, I, or perfluorophenyl; p is an integer from 4 to 6;

D is selected from:

a $C_2$-$C_6$ linear or branched alkoxyl or cycloalkoxyl eventually substituted with one or more groups selected from OH, OR, $NH_2$, NHR, $NR_1R_2$, SH, SR, wherein R, $R_1$, $R_2$ can be equal or different and are selected from H, linear or branched alkyl, cycloalkyl, or aryl;

a $C_2$-$C_6$ linear or branched alkylthio or cycloalkylthio eventually substituted with one or more groups selected from SH, SR, OH, OR, $NH_2$, NHR, $NR_1R_2$, wherein R, $R_1$, $R_2$ can be equal or different and are selected from H, linear or branched alkyl, cycloalkyl, or aryl;

$NR_3R_4$ wherein $R_3$, $R_4$ are equal or different and are selected from H; aryl; $C_1$-$C_{12}$ linear or branched alkyl, the alkyl being eventually substituted with one or more groups selected from: OH, OR, $NH_2$, NHR, $NR_1R_2$, SH, SR, wherein R, R1, R2 are equal or different and are selected from H, linear or branched alkyl, cycloalkyl, or aryl.

The present invention is further directed to radiation curable compositions containing as photoinitiators at least one sulfonium salts of the formula (I) or of the formula (III).

Another object of the present invention is a method for the preparation of the sulfonium salts of formula (I) comprising the following steps:

a) reacting at 0°-100° C. a compound of the formula (IV):

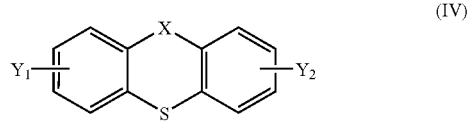

(IV)

wherein X, $Y_1$ and $Y_2$ are the same as in formula (I) with hydrogen peroxide, or with 3-chloro-perbenzoic acid or with an other organic peroxide in glacial acetic acid to give a compound of formula (V):

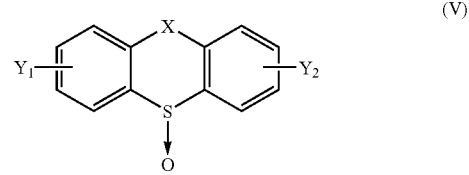

(V)

b) reacting the compound of the formula (V) in the presence of a Lewis acid or a mineral acid with a compound of the formula (IIA):

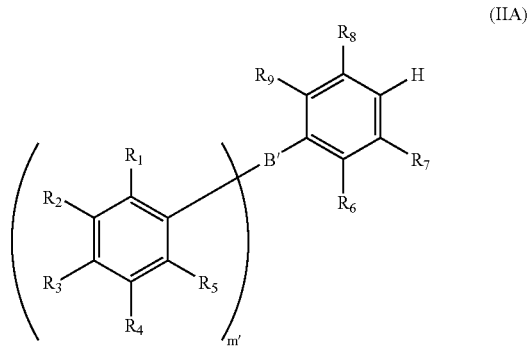

(IIA)

wherein:

$R_1$-$R_9$ are the same as in formula (II); m' is an integer from 0 to 2;

if m'=1 or 2, B' is the same as in formula (II);

if m'=0 B' is halogen;

and if m'=1 the molar ratio of (V)/(IIA) is 2/1 and the thus obtained compound is then reacted with a salt of the formula TZ, wherein T is the cation of an alkaline element and Z is the same as Z in formula (I), to obtain the compounds of the formula (I) wherein m=1 and n=1.

if m'=2 the molar ratio of (V)/(IIA) is 3/1 and the thus obtained compound is then reacted with a salt of formula TZ, wherein T is the cation of an alkaline element and Z is the same as Z in formula (I), to obtain the compounds of the formula (I) wherein m=2 and n=2.

if m'=0 the molar ratio of (V)/(IIA) is 1/1 and the thus obtained compound is then reacted with a salt of formula TZ, wherein T is the cation of an alkaline element and Z is the same as Z in formula (I), to obtain the compounds of formula (IA):

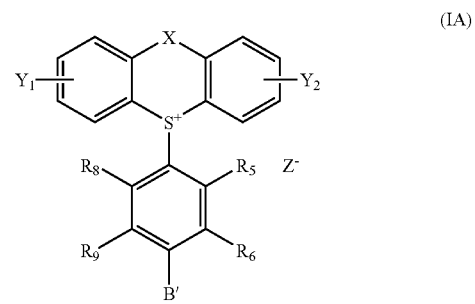

(IA)

wherein $R_6$-$R_9$ are the same as in formula (II).

The preferred Lewis acid is aluminium trichloride; the preferred mineral acid is sulfuric acid.

c) reacting the thus obtained compound of formula (IA) with a compound of formula (IIB):

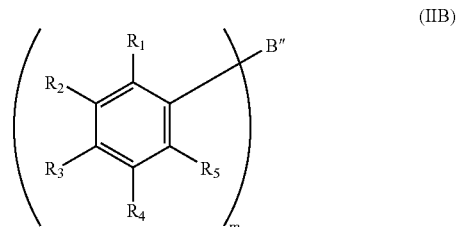

(IIB)

wherein:

$R_1$-$R_5$ are equal or different and are selected from H, halogen atom (F, Cl, Br, I), nitro, $C_1$-$C_6$ linear or branched alkyl, $C_1$-$C_6$ linear or branched alkoxyl, S—$C_1$-$C_6$ linear or branched alkylthio;

m is 1 or 2, and if m=1, B" is selected from: a $C_2$-$C_{18}$ linear or a branched alkylene carrying at one of its end an heteroatom selected from O, S, N—R and at the opposite end a group chosen among NHR, SH, OH, the alkylene being eventually substituted with $C_1$-$C_6$ linear or branched hydroxyalkyl, $C_1$-$C_6$ mercaptoalkyl, hydroxyl, amino, or aminoalkyl; an alicyclic group with two nitrogen atoms in the ring, wherein the first one is linked to the aryl group and the second one is substituted with a hydrogen atom, the alicyclic group being eventually substituted with hydroxyl, amino, $C_1$-$C_6$ linear or a branched aminoalkyl, to obtain the compound of formula (IB):

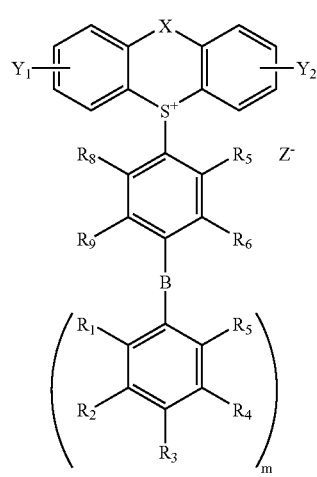

(IB)

wherein m=1 and B, $R_1$-$R_9$, and Z are the same as B, $R_6$-$R_9$ and Z in formula (I).

and

If m=2, B" is selected from: a $C_3$-$C_{18}$ linear or branched alkyl group carrying at its ends two heteroatoms different or equal selected from O, S, N—R, and at the additional end a third group selected from NHR, SH, OH; the alkyl group being eventually substituted with $C_1$-$C_6$ linear or branched hydroxyalkyl or $C_1$-$C_6$ linear or branched mercaptoalkyl, hydroxyl, amino, or aminoalkyl group;

an alicyclic group with two nitrogen atoms linked to the two aryl groups, and a NH, this alicyclic group being eventually substituted with hydroxyl, amino, or $C_1$-$C_6$ linear or a branched aminoalkyl, to obtain the compound of formula (IB) wherein m=2.

d) reacting a compound of formula (IB) and a compound of formula (V) to obtain the compound of formula (I) wherein n is 1 or 2.

Or, after step b):

e) reacting the compound (IA) with a $C_{2\ or\ 3}$-$C_{18}$ linear or branched bi- or trivalent alkyl group substituted with at least 2 or 3 OH, NHR (wherein R is $C_1$-$C_6$ linear or branched alkyl group) or SH in a molar ratio 2/1 or 3/1 to give the compound of formula (I) wherein n is 1 or 2.

Still another object of the present invention is a method for the preparation of the sulfonium salts of formula (III) comprising the following steps:

a) reacting at 0°-100° C. a compound of the formula (IVA):

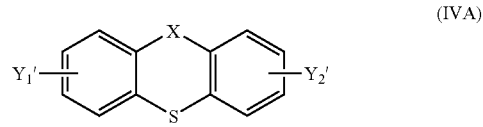

(IVA)

wherein X, $Y_1'$ and $Y_2'$ are the same as in formula (III) with hydrogen peroxide, or with 3-chloro-perbenzoic acid or with an other organic peroxide in acetic acid to give a compound of formula (VA):

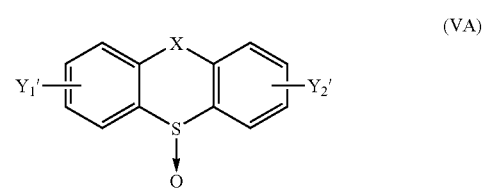

(VA)

b) reacting the thus obtained compound of formula (VA) in the presence of a Lewis acid or a strong mineral acid with a compound of formula (VI):

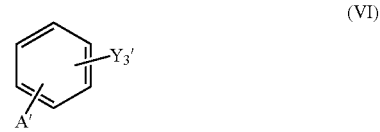

(VI)

wherein A' is a halogen atom (F, Cl, Br, I) and $Y_3'$ is the same as in formula (III);

c) reacting the compound obtained in step b) with a salt of formula LJ, wherein J is the cation of an alkaline element and L is the same as in formula (III), to obtain the compounds of formula (VII):

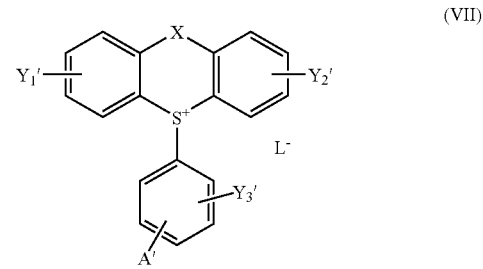

(VII)

d) reacting the compound of formula (VII) with a compound DH, wherein D is the same as in formula (III) to give the compound of formula (III)

DETAILED DESCRIPTION OF THE INVENTION

According to a preferred embodiment of the present invention the compounds of formula (I) are those wherein X is selected from S,CO,$CH_2$, single bond and B is selected from S, single bond, O,

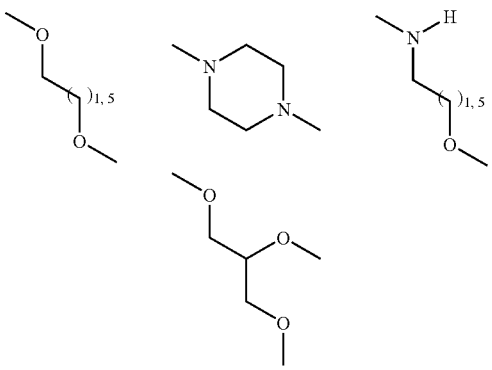

Y is H or $C_1$-$C_6$ linear or branched alkyl.

Particularly preferred compounds of formula (I) are:

4,4'-bis-(thianthrenium-9-yl)-diphenylether dihexafluorophosphate 4,4'-bis-(2,6-dimethyl-thianthrenium-9-yl)-diphenylether dihexafluorophosphate 4,4'-bis-(thianthrenium-9-yl)-diphenylsulfide dihexafluorophosphate 1,2-bis-[4-(thianthrenium-9-yl)-phenoxy]-ethane dihexafluorophosphate 1,4-bis-[4-(thianthrenium-9-yl)-phenyl]-piperazine dihexafluorophosphate 1,2,3-tris-[4-(thianthrenium-9-yl)-phenoxy]-propane trihexafluorophosphate 4,4'-bis-(thianthrenium-9-yl)-diphenyl dihexafluorophosphate 4,4'-bis-(thioxanthenium-10-yl-9-one)-diphenylether dihexafluorophosphate According to another preferred embodiment of the present invention the compounds of formula (III) are those wherein D is:

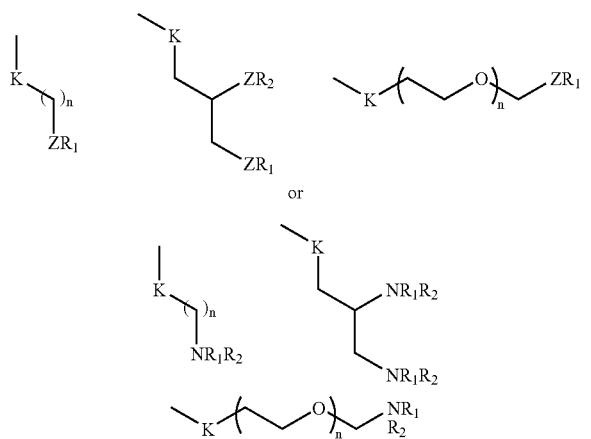

wherein n is an integer from 2 to 10;

K is O, S or $NR_3$ and $R_1$, $R_2$, $R_3$ are equal or different and are selected from H, linear or branched alkyl, cycloalkyl, aryl;

Z is O or S.

Particularly preferred compounds of formula (III) are:
9-[4-(2-hydroxyethoxy)-phenyl]-thiantrenium hexafluorophosphate;
9-[4-(2,3di-hydroxy-propoxy)-phenyl]-thiantrenium hexafluorophosphate.

Preferably, the radiation curable compositions of the present invention contain the sulfonium salts in an amount of from 0.5 to 10%, more preferably of from 0.5 to 5%, w/w.

Advantageously, the sulfonium salts of formula (III) show a good solubility in the formulations and thus they can be added directly to the formulations without being previously dissolved in a solvent.

The radiation curable compositions of the invention polymerise by irradiation at a wavelength of 2000-7000 Angstrom.

Preferably in the radiation curable compositions of the invention the polymerisable compound is a monomer or a pre-polymer belonging to the following categories: epoxides, oxetanes, modified silicones, vegetal epoxidised oil, epoxidised alkenes, cyclic ethers, vinyl ethers (such as ethylvinylether, triethyleneglycol divinylether, 4-epoxybutylvinylether), lactones, styrene, acrolein, vinylarene, vinyl compounds, spiro-ortocarbonate, phenol, formaldehyde.

It is a further object of the present invention to provide liquid formulations containing from 30 to 80% w/w of one or more sulfonium salts of general formula (I) or (III) in a solvent selected from the group consisting of: propylene carbonate, propenyl ether of propylene carbonate (PEPC), γ-butirro-lactone, divinyl ethers, such as ethyl vinyl ether (EVE), n-butyl vinyl ether (n-BVE), 4-hydroxy butyl vinyl ether (HBVE), triethyleneglycol divinyl ether (DVE-3), 1,4-cyclohexanedimethanol-divinyl ether (CHVE) or mixture thereof.

The liquid formulations of the present invention preferably contain propylene carbonate as solvent.

The radiation curable compositions of the invention are utilizable for the coating of food packaging or of metallic surfaces.

Normally, they are polymerised by irradiation with a high or medium pressure mercury lamp or with a Xenon lamp, or a laser or an electron beam.

The exposition time ranges from fractions of seconds to some seconds and it depends on the film thickness and on the intensity of the radiation.

Methods of preparation of sufonium salts are generally well described in many patents such as in U.S. Pat. No. 5,012,001 and in U.S. Pat. No. 4,684,671, where the use of condensation reactions between a reactant bearing a sulfoxide group and another compound, electron rich, able to undergo an electrophilic substitution reaction is described.

Normally a strong mineral acid (e.g. sulfuric acid), eventually in combination with a strong dehydrating agent (e.g. $P_2O_5$), promotes the formation of the electrophilic group.

When the reactivity of the system is low, as in the case of thiantrene, it is suggested to prepare the electrophilic group in the form of perchlorate of the cation-radical; it is reported in literature (Boduszek b. et al., Journal of Organic Chemistry 1989, 54, 1616-1626; Sugiyama K. Et al., Journal of Organic Chemistry, 1983, 48, 143-146) that this electrophilic agent is able to undergo electrophilic substitution reactions with organo metallic Grignard reactants.

Unfortunately the perchlorate of the cation-radical due to its instability is very dangerous.

The Applicant has now found milder reaction conditions to obtain onium salts and, in particular, thiantrenium salts; in the steps a) of the preparation methods of the invention the compounds of formula (IV) and (IVA) are oxidised to obtain the corresponding oxides with an organic peroxide, such as 3-chloroperbenzoic acid, or with an inorganic peroxide, such as hydrogen peroxide, in glacial acetic acid; then, it is possible to obtain the sulfonium salts of the invention by reaction of the oxides with substituted aromatic rings in the presence of a Lewis acid such as aluminium trichloride or of mineral strong acid, such as sulfuric acid.

The following examples are provided to illustrate the present invention. The examples are not intended to limit the scope of the present invention and they should not be so interpreted.

EXAMPLE 1

Thianthrene-9-oxide

To a well stirred solution of thianthrene (22.3 g; 100 mmol) and glacial acetic acid (400 g) at 90° C. was added drop wise hydrogen peroxide 35% (11.3 g; 99.7 mmol) over 55 minutes. After 2 hours 0.5 g of hydrogen peroxide were added and after 30 minutes the mixture was poured into water and the solid was collected by suction filtration and washed with water. The filter cake was dried under vacuum to give a white solid (17.8 g) in a yield of 77% with melting point of 148° C.

1HNMR (CDCl3):δ(ppm):7.39-7.48 (m,2H); 7.52-7.60 (m,2H); 7.61-7.66 (d,2H): 7.91-7.97 (d,2H)

MS:233.1 (M+1)

EXAMPLE 2

4,4'-bis(thianthrenium-9-yl)-diphenylether dihexafluorophosphate

To a solution of diphenylether (3 g), thianthrene-9-oxide (4.06 g) and tetrachloroethylene (200 g) aluminium chloride (7 g) was added in one portion. The suspension was stirred at a gentle reflux for 75 minutes. Then tetrachloroethylene (60 g), thianthrene-9-oxide (4.64 g) and aluminium chloride (8 g) were added maintaining the same condition of reaction. To complete the reaction 0.6 g of thiantrene-9-oxide were further added and the reaction mixture was stirred under reflux for 30 minutes more. The mixture was then poured into water, filtered and washed with ethyl ether. The aqueous phase was added drop wise in a solution of 8.5 g of potassium hexafluorophosphate dissolved in 2 litres of distilled water. The solid precipitated from the solution was collected by suction filtration and washed with water. The filter cake was dried to give a white solid (14.6 g) in a yield of 93.7%.

1HNMR (DMSOd6): δ(ppm):7.16 (d,4H); 7.34 (d,4H); 7.81-7.96 (m,8H); 8.07 (d,4H); 8.54 (d,4H)

MS:745 (M)

EXAMPLE 3

4,4'-bis-(thianthrenium-9-yl)-diphenyl dihexafluorophosphate

A mixture of biphenyl (0.77 g), thianthrene-9-oxide (1.16 g), aluminium chloride (2 g) and tetrachloroethylene (85 g) was stirred at a gentle reflux for 75 minutes. Then tetrachloroethylene (22 g), thianthrene-9-oxide (1.33 g) and aluminium chloride (2.64 g) were added maintaining the same condition. After 75 minutes dilute chloridric acid was added slowly. The extract was treated with a solution of potassium hexafluorophosphate (2.5 g) dissolved in 100 g of water. A white precipitate (0.1 g) was obtained with a m.p. of 140° C.

1HNMR (DMSOd6):δ(ppm):7.28-7.38 (m,4H); 7.76-8.00 (m,12H); 8.01-8.13 (m,4H); 8.55-8.66 (m,4H)

MS:729 (M)

EXAMPLE 4

4,4'-bis-(thianthrenium-9-yl)-diphenylsulfide dihexafluorophosphate a) A mixture of 10 g of fluorobenzene, 0.46 g of thianthrene-9-oxide and 1.6 g of aluminium chloride was stirred at a gentle reflux for 90 minutes. After cooling the mixture was poured into water and the organic phase separated. The aqueous phase was filtered and treated with a solution of 0.5 g of potassium hexafluorophosphate in 10 g of water. The precipitate was filtered off and washed with water, then dried under vacuum to give 0.6 g of a white solid (66%).

1HNMR (DMSOd6):δ(ppm):7.25-7.35 (m,2H); 7.43 (t,2H); 7.82-7.98 (m,4H); 8.08 (d,2H); 8.58 (d,2H)

MS:311 (M)

b) A suspension of 0.14 g of thiophenol in 2.5 ml of a 0.5 N solution of potassium hydroxide in methanol was stirred at reflux for 15 minutes. After cooling 0.57 g of the compound obtained in step a) was added and stirred at room temperature for 60 minutes and then at gentle reflux until the colour was clear. The solvent was removed using a rotary evaporator and the organic phase was dissolved in dichloromethane and washed with water. After drying (Na$_2$SO$_4$) the solvent was removed under vacuum to give 0.7 g of the onium salt as a white solid.

1HNMR (DMSOd6):δ(ppm):7.14 (d,2H); 7.22 (d,2H); 7.47 (bs,5H); 7.78-7.95 (m,4H); 8.06 (dd,2H); 8.57 (dd,2H)

MS:401 (M)

c) 0.23 g of the compound obtained in step b) was added to a mixture of 15 g of 96% sulfuric acid and 0.1 g of thianthrene-9-oxide which was cooled below 10° C. The resulting mixture was stirred for 2.5 hours at room temperature. Then the mixture was poured into a solution of 0.3 g of potassium hexafluorophosphate dissolved in 30 ml of water. A solid precipitated from the solution and was collected by suction filtration. The solid product was dissolved in dichloromethane loaded onto a dry flash chromatographic column (SiO2) and eluted with CH2Cl2 and then with H2O/Toluene/Acetic Acid/Acetone/1-butanol:1,1,1,1,1; 30 mg of 4,4'-bis-(thianthrenium-9-yl)-diphenylsulfide dihexafluorophosphate were obtained.

1HNMR (DMSOd6):δ(ppm):7.20 (d,4H); 7.40 (d,4H); 7.70-8.00 (m,8H); 8.05 (d,4H); 8.55 (d,4H).

EXAMPLE 5

1-oxo-thioxanthen-9-one

To a well stirred solution of 10.3 g of thioxanthen-9-one in 100 ml of glacial acetic acid at 80° C. 5 ml of hydrogen peroxide (35%) was added dropwise. The solution was stirred for 30 minutes, and then concentrated under reduced pressure and additional dichloromethane was added. The organic phase was washed with a solution of sodium hydroxide and then with water. After drying (Na$_2$SO$_4$) the solvent was removed under vacuum and 11 g of an oil were obtained. The oil was purified with a flash chromatography (SiO2) eluting with CH2Cl2 and CH2Cl2/Ethyl acetate 9:1; 8.44 g of a yellow solid were obtained in a yield of 72%.

1HNMR (DMSOd6):δ(ppm):3.81 (d,1 H); 4.32 (d,1H); 7.55 (m,6H); 7.83 (m,2H).
MS:215.2 (M+1)
IR(cm-1): 3057, 2923, 1444, 1085, 1031, 766, 556, 451.

EXAMPLE 6

10-(4-phenoxy-phenyl)-thioxanthenium-9-one hexafluorophosphate

To a suspension of 1.0 g of phenyl ether, 0.20 g of 10-oxo-thioxanthen-9-one and 0.8 g of aluminium chloride 40 g of tetrachloroethylene were added. The suspension was stirred at a gentle reflux for 40 minutes then the organic phase was poured slowly into water and the aqueous phase was washed with ethyl ether. 0.5 g of potassium hexafluorophosphate dissolved in 20 g of water were added to the well stirred aqueous solution. The solid precipitated from the solution was dissolved in dichloromethane, and then the organic phase was separated and dried under vacuum to give 50 mg of a white solid.
1HNMR (DMSOd6):δ(ppm):4.22 (d,1H); 4.55 (d,1H); 7.08 (d,2H); 7.15 (d,2H); 7.25 (t,1H); 7.44 (t,2H); 7.52 (d(2H); 7.76-7.65 (m,2H); 7.87-7.79 (m,4H); 8.29 (d,2H).
MS:367.2 (M)

EXAMPLE 7

4,4'-bis-(thioxantenium-10-yl-9-one)-diphenylether dihexafluorophosphate

To a mixture of 0.50 g of 10-(4-phenoxy-phenyl)-thioxanthenium-9-one hexafluorophosphate, 0.3 g of 10-oxo-thioxanthen-9-one and 0.40 g of aluminium chloride were dissolved in 80 g of tetrachloroethylene at room temperature. The solution was stirred for 30 minutes, then 0.43 g of aluminium chloride were added; after 20 minutes 0.17 g of 10-(4-phenoxy-phenyl)-thioxanthenium-9-one hexafluorophosphate, and 0.34 g of aluminium chloride were added and the reaction mixture was then stirred for 15 minutes. The organic phase was poured into water and the aqueous phase was washed with ethyl ether. 0.30 g of potassium hexafluorophosphate dissolved into 10 g of water were added to the solution to give a deep yellow solid (0.25 g).
1HNMR (DMSOd6):δ(ppm):4.25 (d,1H); 4.62 (d,1H); 7.25 (d,4H); 7.50 (d,4H); 7.76-7.40 (m,4H); 7.95-7.78 (m,12H); 8.34 (d,4H).
MS:709.2 (M)

EXAMPLE 8

9-(4-fluoro-phenyl)-thianthrenium hexafluorophosphate

A reaction flask was charged with 10 g (104.2 mmol) of fluorobenzene, 0.46 g (1.98 mmol) of thianthrene-9-oxide and 1.6 g (12.03 mmol) of aluminium chloride. The reaction mixture was stirred at reflux for 90 minutes. After cooling the mixture was poured into water and the organic layer was separated. Potassium hexafluorophosphate dissolved in 10 g of water was added to the solution. The mixture was stirred and a crystalline product was obtained by filtration. The filtrate was washed with water and then dried under vacuum to give 0.6 g (66%) as a white solid.
1HNMR (DMSOd6):δ(ppm):7.25-7.35 (m,2H); 7.43 (t,2H); 7.82-7.98 (m,4H);8.08, (d,2H); 8.58 (d,2H).
MS:311 (M)

EXAMPLE 9

9-[4-(2-hydroxyethoxy)-phenyl]-thianthrenium hexafluorophosphate

A round bottom flask was charged with 0.2 g (0.438 mmol) of 9-(4-fluoro-phenyl)-thianthrenium hexafluorophosphate, and 5.0 g of ethylene glycol. The mixture was heated up to 120° C. and stirred until complete dissolution. 50 mg of potassium hydroxide were added to this solution; the solution was stirred for 1 hour and then poured into water. Dichloromethane was added and the organic layer separated, washed with water and dried (Na$_2$SO$_4$). After drying the solvent was removed under vacuum to give a white solid (0.2 g, 92%).
1HNMR (DMSOd6):δ(ppm):3.62 (m,2H); 4.00 (t,2H); 7.10 (d,2H); 7.75 (m,4H); 8.05 (d,2H); 8.50 (d,2H).
MS:353 (M)

EXAMPLE 10

9-[4-(2,3-dihydroxy-propoxy)-phenyl]-thianthrenium hexafluorophosphate

To a 3 necked round bottom flask 0.2 g (438.6 mmol) of 9-(4-fluoro-phenyl)-thianthrenium hexafluorophosphate and 10 g of glycerol were added. The suspension was stirred at 120° C. until complete dissolution. Then 50 mg of potassium hydroxide were added and stirred for 10 minutes and the mixture was poured into water. Dichloromethane was added and the organic layer was washed and dried (Na$_2$SO$_4$). Removal of the solvent under vacuum gave a white solid (0.17 g, 73.4%).
1HNMR (DMSOd6):δ(ppm):3.35-3.45 (m,2H); 3.70-3.85 (m,1H); 3.90-4.10 (m,2H); 7.13 (d,2H); 7.50 (d,2H); 7.75-7.95 (m,4H); 8.05 (d,2H); 8.45 (d,2H).
MS:383 (M)

EXAMPLE 11

2,6-dimethyl-9-(4-phenoxy-phenyl )-thianthrenium hexafluorophosphate

A reaction flask was charged with 2.0 g (7.69 mmol) of 2,6-dimethyl-thianthrene-9-oxide and 18 g of biphenyl. The reaction mixture was stirred at 70° C. and then 7 g of aluminium chloride were added in 1 hour. 2 g of aluminium chloride were then further added. The solution was cooled and poured in 600 ml of water and then washed with ethyl ether. 1.58 g of potassium hexafluorophosphate dissolved in water and 200 ml of dichloromethane were added to this solution. The mixture was vigorously stirred for 1 hour then the organic layer was separated, washed and dried (Na$_2$SO$_4$). Removal of the solvent under vacuum gave 2.59 g (60%) of a solid.
1HNMR (DMSOd6):δ(ppm):8.38 (t,2H); 7.92 (t,2H); 7.73 (d,1H); 7.64 (d,1H); 7.44 (t,2H); 7.31 (d,2H); 7.25 (t,1H); 7.11 (d,2H); 7.06 (d,2H); 2.5 (s,3H).
MS:413.3 (M+1)

EXAMPLE 12

9-(4-phenoxy-phenyl)-dibenzothiophenium hexafluorophosphate

A round bottom flask was charged with 1.72 g of phenyl ether (10 mmol), 2.0 g of dibenzothiophene-9-oxide (10 mmol), 4.0 g of aluminium chloride (30 mmol) and 90 g of tetrachloroethylene. The mixture was heated at reflux for 75 minutes, diluted with water (70 g) separated and the resulting cloudy aqueous solution was filtered and added to a solution of 3.0 g of potassium hexafluorophosphate. The solid precipitated from solution was collected by suction filtration, washed and dried (0.60 g).

1HNMR (DMSOd6):δ(ppm):8.49 (d,2H); 8.33 (d,2H); 7.96 (t,3H); 7.76 (t,3H); 7.67-7.55 (m,3H); 7.49-7.40 (m,1H); 7.32-7.19 (m,1H); 7.10 (d,2H).

MS=353.2 (M)

EXAMPLE 13

9-(4-phenylthio-phenyl)-dibenzothiophenium hexafluorophosphate

A mixture of dibenzothiophene-9-oxide (2.0 g 10 mmol), diphenyl sulfide (1.90 g, 10 mmol), aluminium chloride (4.0 g, 30 mmol) and tetrachloroethylene (100 g) was stirred at gentle reflux for 75 minutes. After cooling the mixture was separated, filtered off and added to a solution of 3.0 g of potassium hexafluorophosphate in 40 g of water. The solid precipitated from the solution was collected by suction filtration, washed with water and dried to give a light yellow solid (0.75 g).

MS=369.2 (M)

EXAMPLE 14

9-(4-fluoro-phenyl)-dibenzothiophenium hexafluorophosphate

A reaction flask was charged with 2.5 g of dibenzothiophene-9-oxide (12.5 mmol), 50 g of fluorobenzene and stirred at room temperature. 10 g of aluminium chloride (75 mmol) were added in 5 minutes. The suspension was stirred at reflux for 90 minutes. After cooling water was added and the mixture was separated and filtered. 3.3 g of potassium hexafluorophosphate dissolved in 100 g of water and dichloromethane were added to the aqueous solution. The organic layer was separated and the solvent removed to give a white solid (40 mg).

1HNMR (DMSOd6):δ(ppm):8.5 (d,2H); 8.35 (dd,2H); 7.97 (t,2H); 7.82-7.67 (m,4H); 7.45 (t,2H).

MS=279.2 (M)

EXAMPLE 15

4,4'-bis-(isopropyl-thioxanthenium-10-yl-9-one)-diphenylether dihexafluorophosphate mixture of 2- and 4-isomers 0.54 g (2 mmol) of isopropyl-10-oxo-thioxanthen-9-one mixture of 2- and 4-isomers were slowly added while stirring to 26 g of concentrated sulfuric acid cooled to 5° C. After 1 hour 0.35 g (2 mmol) of phenyl ether were added to the mixture. The mixture was then stirred the night at room temperature and then poured into water and washed with ethyl ether. 0.50 g (2.72 mmol) of potassium hexafluorophosphate dissolved in 20 g of water and dichloromethane were added to this solution. The mixture was stirred and the dichloromethane layer was separated, the solvent was removed using a rotary evaporator and a deep yellow solid (200 mg) was obtained.

1HNMR (DMSOd6):δ(ppm):8.56 (s,2H); 8.42 (s,2H); 8.20-7.90 (m,6H); 7.70 (d,4H); 7.15 (d,4H); 7.05 (d,4H); 3.20 (s,2H); 1.30 (d,12H).

MS=821.2 (M)

EXAMPLE 16

4,4'-bis-(2,6-dimethyl-thianthrenium-9-yl)-diphenylether dihexafluorophosphate A mixture of 0.30 g (0.54 mmol) of 2,6-dimethyl-9-(4-phenoxy-phenyl)-thianthrenium hexafluorophosphate, 0.15 g (0.59 mmol) of 2,6-dimethyl-thiantren-9-oxide, 70 g of tetrachloroethylene and 0.21 g (1.61 mol) of aluminium chloride was stirred at room temperature for 40 minutes. 1 g (3.84 mmol) of 2,6-dimethyl-thiantren-9-oxide was added, the mixture was stirred for 1 hour and then poured into water and washed with dichloromethane. Potassium hexafluorophosphate dissolved in water was added to this solution and the solid precipitated was filtered and dried to give 40 mg of a solid.

1HNMR (DMSOd6):δ(ppm):8.40 (d,2H); 7.90 (t,2H); 7.75 (d,1H); 7.65 (d,1H); 7.30 (d,2H); 7.15 (d,2H); 2.5 (s,6H).

MS=801.2 (M)

The sulfonium salts prepared as described in the examples were tested in radiation curable compositions to measure their reactivity and the concentration of low molecular weight fragmentation products (benzene in particular) released during irradiation.

The photoinitiator of Example 2 was dissolved in propylene carbonate to obtain a 50% w/w solution. The thus obtained solution was added to a composition (Composition A') of 81,5 parts of 3,4-di-epoxycyclohexyl-methyl-3',4'-epoxycyclohexandicarboxylate, 17 parts of triethyleneglycol divinylether and 1.5 parts of a non-ionic fluoroaliphatic polymeric ester to obtain two radiation curable compositions containing the photoinitiator in the desired amount (0.5 and 4% w/w). The reference radiation curable composition (Composition A) contained as photoinitiator a mixture of bis-[4-(diphenylsulfonio)-phenyl]-sulfide dihexafluorophosphate and was prepared by adding to Composition A' a 50% solution of said photoinitiator in propylene carbonate.

The resulting radiation curable compositions were spread on an aluminium support as a 12 micron thick film and irradiated with a high-pressure mercury lamp having energy of 700 mJ.

The samples, when treated with a thermal post curing, were maintained at 105° C. for 10 minutes.

The tests were performed with a Sheen scratch test apparatus, measuring the hardness of the polymerised coating; the number of pendulum passages needed to completely scratch the coating was measured; this test was performed with pendulums of different weight (Scratch Test)

The results are reported in the following table.

TABLE 1

| | | | Scratch Test | | |
|---|---|---|---|---|---|
| Radiation curable composition | Photo-initiator % | Thermal post-curing | No. of passages with a 75 g pendulum | No. of passages with a 100 g pendulum | No. of passages with a 200 g pendulum |
| Composition A | 4 | Yes | >50 | 23 | 12 |
| Composition containing the compound of Example 2 | 4 | Yes | 33 | 20 | 18 |

TABLE 1-continued

Scratch Test

| Radiation curable composition | Photo-initiator % | Thermal post-curing | No. of passages with a 75 g pendulum | No. of passages with a 100 g pendulum | No. of passages with a 200 g pendulum |
|---|---|---|---|---|---|
| Composition containing the compound of Example 2 | 0.5 | Yes | 46 | 30 | 18 |

The photoinitiator of Example 9 was directly dissolved in Composition A' to obtain two radiation curable compositions containing the photoinitiator in the desired amount (2 and 4%).

These radiation curable compositions were tested with the "single passage scratch test", measuring the minimum weight of the pendulum needed to completely scratch the coating with one single passage.

Composition A was again used as the reference.

The results are reported in Table 2.

TABLE 2

Single passage scratch test.

| Radiation curable composition | Photoinitiator % | Pendulum weight (g) |
|---|---|---|
| Composition A | 4 | 1200 |
| Composition containing the compound of Example 9 | 2 | 1200 |
| Composition containing the compound of Example 9 | 4 | 1400 |

The photoinitiator of Example 9 was then dissolved in propylene carbonate to obtain a 50% w/w solution. The solution was added to Composition A' to obtain a radiation curable composition containing 4% by weight of the photoinitiator.

Compostion A (containing 4% of photoinitiator) was again used as the reference. The results are reported in Table 3.

TABLE 3

Scratch test.

| Radiation curable composition | Thermal post-curing | No. of passages with a 75 g pendulum | No. of passages with a 100 g pendulum | No. of passages with a 200 g pendulum |
|---|---|---|---|---|
| Composition A | No | 23 | 12 | 7 |
| Composition containing the compound of Example 9 | No | 34 | 24 | 11 |
| Composition A | Yes | 29 | 17 | 9 |
| Composition containing the compound of Example 9 | Yes | >50 | 40 | 21 |

As can be seen, the sulfonium salts of the invention possess a reactivity that is similar or greater of the reference.

To evaluate the release of low molecular weight organic compounds the content of benzene in the polymerised radiation curable compositions (containing 4% of photoinitiator) was measured. The content of benzene was determined by headspace GC, a capillary column CP-select 624 CB, 30 m×0.32 mm id, film 1.8 μm and FID detector at 250° C. The samples were cut into small pieces, charged in a head space vial containing DMSO, then warmed up for 30' at 95° C. and injected (2,5 ml)

The results are reported in Table 4.

TABLE 4

| Radiation curable composition | Thermal Post Curing | Benzene (ppm) |
|---|---|---|
| Composition A | Yes | 178 |
| Composition A | No | 60 |
| Composition containing the compound of Example 2 | Yes | <1 |
| Composition containing the compound of Example 9 | Yes | <1 |
| Composition A (without photoinitiator) | — | <1 |

The invention claimed is:

1. Sulfonium salts of the general formula (I):

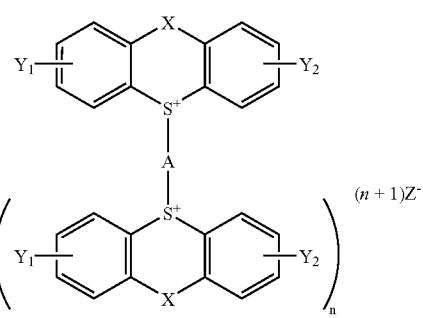

wherein: n is 1 or 2;
X is selected from: S, O, CH$_2$, CO, single bond, N—R wherein R is H, or alkyl or aryl;
Y$_1$ and Y$_2$ are equal or different and are selected from: H, C$_1$-C$_6$ linear or branched alkyl, cycloalkyl, O-alkyl, hydroxyl, halogen, S-alkyl, S-aryl;
Z$^-$ is a group of the general formula MQ$_p$ wherein M is B, P, As, or Sb;
Q is F, Cl, Br, I, or perfluorophenyl;
p is an integer from 4 to 6;
A is a functional group of the general formula (II):

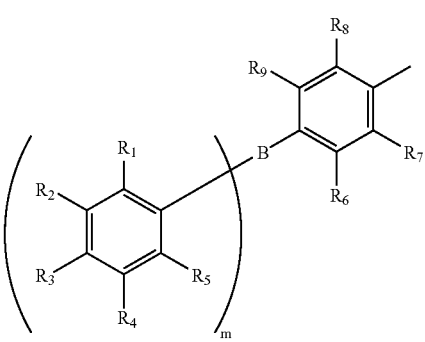

carrying two or three sulfonium salts units, wherein: m is 1 or 2;
R₁-R₉ are equal or different and are selected from: single bond, H, halogen atom (F, Cl, Br, I), nitro, $C_1$-$C_6$ linear or branched alkyl, $C_1$-$C_6$ linear or branched alkoxyl, S—$C_1$-$C_6$ linear or branched alkylthio, with the proviso that at least one of R,—$R_5$ is H;

when m=1, B is selected from: O; S; SO;$SO_2$; $CH_2$; single bond; NR (wherein R is H, $C_1$-$C_6$ linear or branched alkyl); $C_1$-$C_{18}$ linear or branched alkylene carrying at its ends two heteroatoms, equal or different, selected from O, S, N—R the alkylene 15 being eventually substituted with $C_1$-$C_6$ linear or branched hydroxyalkyl, $C_1$-$C_6$ linear or branched mercaptoalkyl, hydroxyl, amino or aminoalkyl; an alicyclic group containing two nitrogen atoms in the ring, the alicyclic group being eventually substituted with OH, $NH_2$, $C_1$-$C_6$ linear or branched aminoalkyl;

when m=2, B is selected from N; a $C_3$-$C_{18}$ linear or branched alkyl carrying three heteroatoms, equal or different selected from O, S, N—R, the alkyl being eventually substituted with $C_1$-$C_6$ hydroxyalkyl, $C_1$-$C_6$ mercaptoalkyl, hydroxyl, amino or aminoalkyl; an alicyclic group with three N in the ring, the alicyclic group being eventually substituted with OH, $NH_2$, $C_1$-$C_6$ linear or branched aminoalkyl.

2. Sulfonium salts according to claim 1, wherein X is selected from S, CO, CH2, single bond and B is selected from S, single bond, O,

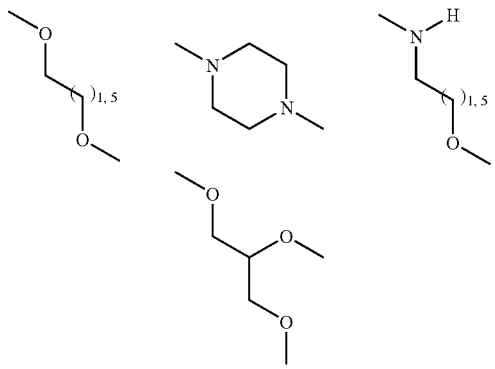

Y is H or $C_1$-$C_6$ linear or branched alkyl.

3. Sulfonium salts according to claim 1, characterized by the fact that they are selected from the group consisting of:
4,4'-bis-(thianthrenium-9-yl)-diphenylether dihexafluorophosphate
4,4'-bis-(2,6-dimethyl-thianthrenium-9-yl)-diphenylether dihexafluorophosphate
4,4'-bis-(thianthrenium-9-yl)-diphenylsulfide dihexafluorophosphate
1,2-bis-[4-(thianthrenium-9-yl)-phenoxy]-ethane dihexafluorophosphate
1,4-bis-[4-(thianthrenium-9-yl)-phenyl]-piperazine dihexafluorophosphate
1,2,3-tris-[4-(thianthrenium-9-yl)-phenoxy]-propane trihexafluorophosphate
4,4'-bis-(thianthrenium-9-yl)-diphenyl dihexafluorophosphate
4,4'-bis-(thioxanthenium-10-yl-9-one)-diphenylether dihexafluorophosphate.

4. Sulfonium salts of the general formula (III):

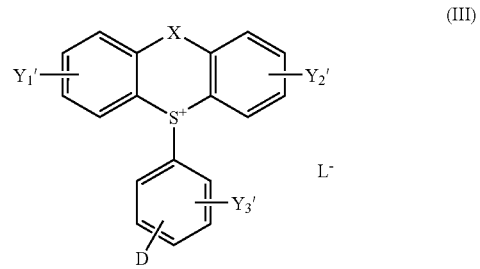

(III)

wherein:
X is selected from: S, O, $CH_2$, CO, single bond, N—R wherein R is H, or alkyl or aryl;

$Y_1'$, $Y_2'$, $Y_3'$ are equal or different and are selected from: H, $C_1$-$C_6$ linear or branched alkyl, cycloalkyl, O-alkyl, hydroxyl, halogen, S-alkyl, S-aryl, $NR_1R_2$ wherein $R_1$ and $R_2$ are equal or different and are selected from H, linear or branched alkyl, cycloalkyl, aryl;

$L^-$ is a group of the general formula $MQ_p$ wherein M is B, P, As or Sb;

Q is F, Cl, Br, I, or perfluorophenyl;

p is an integer from 4 to 6;

D is selected from:

a $C_2$-$C_6$ linear or branched alkoxyl or cycloalkoxyl eventually substituted with one or more groups selected from OH, OR, $NH_2$, NHR;

a $C_2$-$C_6$ linear or branched alkylthio or cycloalkylthio eventually substituted with one or more groups selected from SH, SR, OH, OR, $NH_2$, NHR, $NR_1R_2$, wherein R, R1, and $R_2$ can be equal or different and are selected from H, linear or branched alkyl, cycloalkyl, or aryl;

$NR_3R_4$ wherein $R_3$, $R_4$ are equal or different and are selected from H; aryl; $C_1$-$C_{12}$ linear or branched alkyl, the alkyl being eventually substituted with one or more groups selected from: OH, OR, $NH_2$, NHR, $NR_1R_2$, SH, SR, wherein R, $R_1$, and $R_2$ can be equal or different and are selected from H, linear or branched alkyl, cycloalkyl, or aryl.

5. Sulfonium salts according to claim 4, wherein D is:

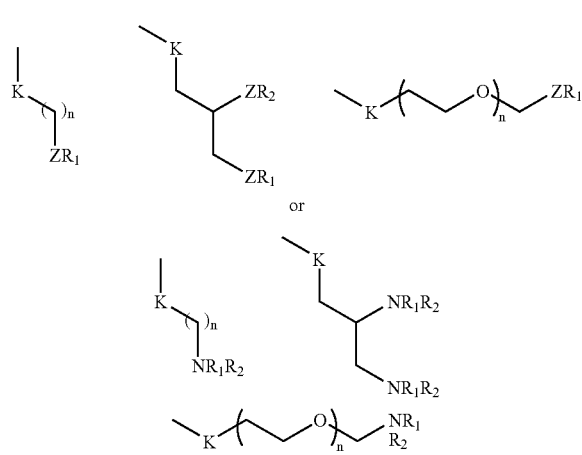

wherein n is an integer from 2 to 10;

K is O, S or $NR_3$ and $R_1$, $R_2$, and R3 are equal or different and are selected from H, linear or branched alkyl, cycloalkyl, aryl;

Z is O or S.

6. Sulfonium salts according to claim 4, wherein the sulfonium salts are selected from the group consisting of:

9-[4-(2-hydroxyethoxy)-phenyl] thiantrenium hexafluorophosphate; and

9-[4-(2,3-di-hydroxy-propoxy)-phenyl] thiantrenium hexafluorophosphate.

7. Radiation curable compositions containing a photoinitiator wherein the photoinitiator is a sulfonium salt of Glaime claim 1.

8. The radiation curable compositions of claim 7, wherein the radiation curable compositions includes from 0.5 to 10% w/w of the sulfonium salt.

9. The radiation curable compositions claim 7, wherein the radiation curable compositions includes from 0.5 to 5 % w/w of the sulfonium salt.

10. The radiation curable compositions claim 7, wherein the radiation curable compositions polymerize by irradiation at a wavelength of 2000-7000 Angstrom.

11. The radiation curable compositions of claim 7, wherein the radiation curable compositions contain as the polymerizable compound monomers or a pre-polymers belonging to the following categories: epoxides, oxetanes, modified silicones, vegetal epoxidised oil, epoxidised alkenes, cyclic ethers, vinyl ethers, lactones, styrene, acrolein, vinylarene, vinyl compounds, spiro-ortocarbonate, phenol, formaldehyde.

12. The radiation curable compositions of claim 11, wherein the radiation curable compositions contain as the polymerizable compound 3,4-di-epoxycyclohexyl-methyl-3', 4'-epoxycyclohexandi carboxylate.

13. Liquid formulations containing from 30 to 80% w/w of one or more of the sulfonium salts of claim 1 and a solvent selected from the group consisting of propylene carbonate, propenyl ether of propylene carbonate (PEPO), γ-butirrolactone, divinyl ethers, and mixtures thereof.

14. The liquid formulations of claim 13, wherein the divinyl ethers are selected from the group consisting of: ethyl vinyl ether (EVE), n-butyl vinyl ether (n-BVE), 4-hydroxy butyl vinyl ether (HBVE), triethyleneglycol divinyl ether (DVE-3), and 1,4-cyclohexane-dimethanol-divinyl ether (CHVE).

15. The liquid formulations of claim 13, wherein the solvent is propylene carbonate.

16. A method for the preparation of the sulfonium salts of claim 1 comprising the steps of:

a) reacting at 0°-100° C. a compound of the formula (IV):

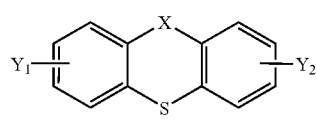
(IV)

wherein X and $Y_1$ and $Y_2$ are the same as in formula (I) with hydrogen peroxide, or with 3-chloro-perbenzoic acid or with an other organic peroxide in glacial acetic acid to give a compound of formula (V):

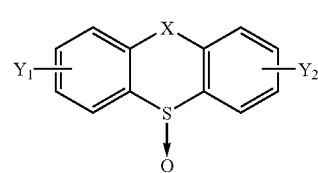
(V)

b) reacting the compound of the formula (V) in the presence of a Lewis acid or a mineral acid with a compound of the formula (IIA):

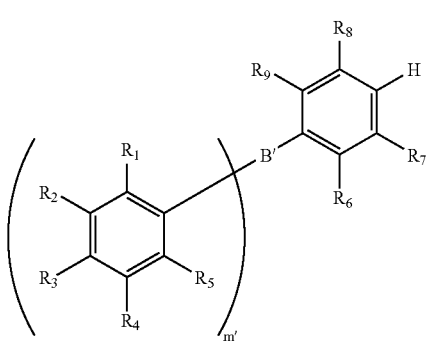
(IIA)

wherein: $R_1$-$R_9$ are the same as in formula (II); m' is an integer from 0 to 2;
if m'=1 or 2, B' is the same as in formula (II); if m'=0, B' is halogen; and
if m'=1 the molar ratio of (V)/(IIA) is 2/1 and the thus obtained compound is then reacted with a salt of the formula TZ, wherein T is the cation of an alkaline element and Z is the same as Z in formula (I), to obtain the compounds of the formula (I) wherein m=1 and n=1,
if m'=2 the molar ratio of (V)/(IIA) is 3/1 and the thus obtained compound is then reacted with a salt of formula TZ, wherein T is the cation of an alkaline element and Z is the same as Z in formula (I), to obtain the compounds of the formula (I) wherein m=2 and n=2,
if m'=0 the molar ratio of (V)/(IIA) is 1/1 and the thus obtained compound is then reacted with a salt of formula TZ, wherein T is the cation of an alkaline element and Z is the same as Z in formula (I), to obtain the compounds of formula (IA):

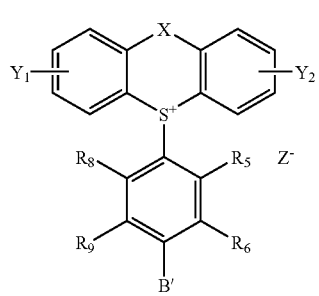
(IA)

wherein
$R_6$-$R_9$ are the same as in formula (II);
the preferred Lewis acid is aluminium bichloride; the preferred mineral acid is sulfuric acid;

c) reacting the thus obtained compound of formula (IA) with a compound of the formula (IIB):

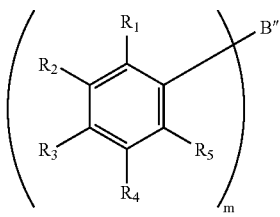

wherein:
$R_1$-$R_5$ are equal or different and are selected from H, halogen atom (F, Cl, Br, I), nitro $C_1$-$C_6$ linear or branched alkyl, $C_1$-$C_6$ linear or branched alkoxyl, S—$C_1$-$C_6$ linear or branched alkylthio;
m is 1 or 2, and
if m=1, B" is selected from: a $C_1$-$C_{18}$ linear or a branched alkylene carrying at one of its end an heteroatom selected from O, S, N—R and at the opposite end a group chosen among NHR, SH, OH, the alkylene being eventually substituted with $C_1$-$C_6$ linear or branched hydroxyalkyl, $C_1$-$C_6$ mercaptoalkyl, hydroxyl, amino, or aminoalkyl; an alicyclic group with two nitrogen atoms in the ring, wherein the first one is linked to the aryl group and the second one is substituted with a hydrogen atom, the alicyclic group being eventually substituted with hydroxyl, amino, $C_1$-$C_6$ linear or a branched aminoalkyl,
to obtain the compound of formula (IB):

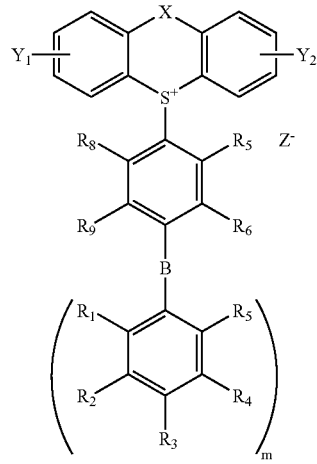

wherein m=1 and B, $R_1$-$R_9$, and Z are the same as B, $R_6$-$R_9$ and Z in formula (I), and
If m=2, B" is selected from: a $C_1$-$C_6$ linear or branched alkyl group carrying at its ends two heteroatoms different or equal selected from O, S, N—R, and at the additional end a third group selected from NHR, SH, OH; the alkyl group being eventually substituted with $C_1$-$C_6$ linear or branched hydroxyalkyl or $C_1$-$C_6$ linear or branched mercaptoalkyl, hydroxyl, amino, or to a aminoalkyl group; an alicyclic group with two nitrogen atoms linked to the two aryl groups, and a NH, this alicyclic group being eventually substituted with hydroxyl, amino, or $C_1$-$C_6$ linear or a branched aminoalkyl, to obtain the compound of formula (IB) wherein m=2;
d) reacting a compound of formula (IB) and a compound of formula (V) to obtain the compound of formula (1) wherein n is 1 or 2; or, after step b):
e) reacting the compound (IA) with a $C_{2\ or\ 3}$-$C_{18}$ linear or branched bi- or trivalent alkyl group substituted with at least 2 or 3 OH, NHR (wherein R is $C_1$-$C_6$ linear or branched alkyl group) or SH in a molar ratio 2/1 or 3/1 to give the compound of formula (1) wherein n is 1 or 2.

17. The method for the preparation of the sulfonium salts of claim 16, wherein in step a) the organic peroxide is 3-chloro perbenzoic acid.

18. The method for the preparation of the sulfonium salts of claim 16, wherein in step b) the Lewis acid is aluminium bichloride.

19. The method for the preparation of the sulfonium salts of claim 16, wherein in step b) the mineral acid is sulfuric acid.

20. A method for the preparation of the sulfonium salts of claim 4 comprising the steps of:
a) reacting at 0°-100° C. a compound of formula (IVA):

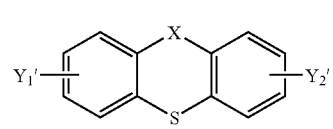

wherein X, $Y_1'$ and $Y_2'$ are the same as in formula (Ill) with hydrogen peroxide, or with 3-chloro-perbenzoic acid or with another organic peroxide in acetic acid to give a compound of formula (VA):

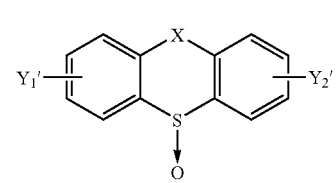

b) reacting the thus obtained compound of formula (VA) in the presence of a Lewis acid or a strong mineral acid with a compound of formula (VI):

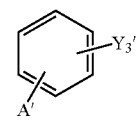

wherein A' is a halogen atom (F, Cl, Br, I) and $Y_3'$ is the same as in formula (Ill);
c) reacting the compound obtained in step b) with a salt of formula LJ, wherein J is the cation of an alkaline element and L is the same as in formula (Ill), to obtain the compounds of formula (VII):

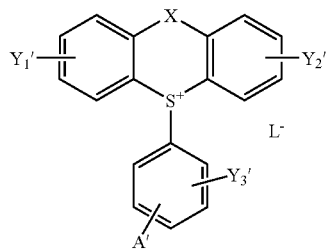

(VII)

reacting the compound of formula (VII) with a compound DH, wherein D is the same as in formula (Ill) to give the compound of formula (Ill).

21. The method for the preparation of sulfonium salts according to claim 20 wherein in step a) the organic peroxide is 3-chloro perbenzoic acid.

22. The method for the preparation of sulfonium salts according to claim 20 wherein in step b) the Lewis acid is aluminium bichloride.

23. The method for the preparation of sulfonium salts according to claim 20 wherein in step b) the mineral acid is sulfuric acid.

24. The radiation curable compositions of claim 11, wherein the vinyl ether is selected from the group consisting of ethylvinylether, triethyleneglycol, divinylether, and 4-epoxybutylvinylether.

* * * * *